(12) United States Patent
Considine et al.

(10) Patent No.: US 7,601,847 B2
(45) Date of Patent: Oct. 13, 2009

(54) PREPARATION AND PURIFICATION OF 4-(INDAZOL-3-YL)PHENOLS

(75) Inventors: John Leo Considine, Bridgewater, NJ (US); Galina Vid, New City, NY (US); Zhixian Ding, Fort Lee, NJ (US)

(73) Assignee: Wyeth, Madison, NJ (US)

( * ) Notice: Subject to any disclaimer, the term of this patent is extended or adjusted under 35 U.S.C. 154(b) by 520 days.

(21) Appl. No.: 11/257,344

(22) Filed: Oct. 24, 2005

(65) Prior Publication Data

US 2006/0111574 A1   May 25, 2006

Related U.S. Application Data

(60) Provisional application No. 60/622,240, filed on Oct. 26, 2004.

(51) Int. Cl.
*C07D 231/56* (2006.01)
(52) U.S. Cl. .................................. 548/361.1
(58) Field of Classification Search .............. 548/361.1
See application file for complete search history.

(56) References Cited

U.S. PATENT DOCUMENTS

| | | | |
|---|---|---|---|
| 4,042,704 A | 8/1977 | Coombs | 514/406 |
| 5,296,604 A | 3/1994 | Hanko et al. | 546/169 |
| 2002/0173663 A1 | 11/2002 | Liu et al. | 548/207 |
| 2003/0176421 A1 | 9/2003 | Watson et al. | 514/224.2 |

FOREIGN PATENT DOCUMENTS

| | | |
|---|---|---|
| EP | 0 516 982 A1 | 12/1992 |
| EP | 0 638 572 A1 | 2/1995 |
| EP | 0 816 357 A1 | 1/1998 |
| EP | 0 915 089 A2 | 5/1999 |
| EP | 0 995 439 A1 | 4/2000 |
| EP | 1 040 829 A2 | 10/2000 |
| JP | 2000128785 A2 | 5/2000 |
| JP | 2000198734 A2 | 7/2000 |
| WO | 94/07847 A1 | 4/1994 |
| WO | 95/00509 A1 | 1/1995 |
| WO | 97/06164 A1 | 2/1997 |
| WO | 97/42174 A1 | 11/1997 |
| WO | 97/49702 A1 | 12/1997 |
| WO | 98/03504 A1 | 1/1998 |
| WO | 98/09961 A1 | 3/1998 |
| WO | 98/21210 A1 | 5/1998 |
| WO | 99/23076 A1 | 5/1999 |
| WO | 99/23077 A1 | 5/1999 |
| WO | 99/54295 A1 | 10/1999 |
| WO | 00/63207 A1 | 10/2000 |
| WO | 01/60807 A1 | 8/2001 |
| WO | WO02/10137 * | 2/2002 |
| WO | 02/22586 A1 | 3/2002 |
| WO | 02/083648 A1 | 10/2002 |
| WO | 03/035654 A1 | 5/2003 |
| WO | 03/062392 A2 | 7/2003 |
| WO | 03/070236 A2 | 8/2003 |
| WO | WO2004/031159 * | 4/2004 |

OTHER PUBLICATIONS

Ozol et al. Chemistry of Heterocyclic Compound, 1975, 11(11):p. 1315-1317.*
Hernandez et al. (J.Org. Chem. 2004, 69: p. 3590-3592.*
Fujimura et al. Heterocycles. 1986, 24(10):p. 2771-2775.*
Cline et al. J. Org. Chem. 1978, 43(26): p. 4910.*
Abiko, A. et al., "New Isoxazolidine-based Chiral Auxiliaries for Asymmetric Syntheses," *Tetrahedron Letters*, 1997, 38(18), 3261-3264.
Alpegiani, M. et al., "2-Selenacephems and 1-Dethia-1-Selenapenems," *Tetrahedron Letters*, 1986, 27(26), 3041-3044.
Alvarez-Ibarra, C. et al., "Diastereoselective synthesis and estimation of the conformational flexibility of 6-oxoperhydropyridazine-3-carboxylic acid derivatives," *Journal of Organic Chemistry*, 2002, 67(9), 2789-2797.
Andrews, D. et al., "Design and synthesis of spiro-cyclopentenyl and spiro-[1,3]-dithiolanyl substituted pyrrolidine-5,5-trans-lactams as inhibitors of hepatitis C virus NS3/4A protease," *Bioorganic & Medicinal Chemistry Letters*, 2003, 13(10), 1657-1660.
Angell, R. et al., "Novel Chiral Templated for 1,3-Oxazolium-4-olate (isomünchnone) Cycloadditions: (5R)- and (5S)-Phenyloxazin-2,3-dione," *Tetrahedron Letters*, 1997, 38(17) 3107-3110.
Artman III, G. et al., "An approach to the total synthesis of the marine ascidian metabolite perophoramidine via a halogen-selective tandem Heck/carbonylation strategy," *Organic Letters*, 2003, 5(9), 1523-1526.
Ashwood, V. et al., "Utilization of an intramolecular hydrogen bond to increase the CNS penetration of an NK(1) receptor antagonist," *Journal of Medicinal Chemistry*, 2001, 44(14), 2276-2285.

(Continued)

*Primary Examiner*—Kamal A Saeed
*Assistant Examiner*—Valerie Rodriguez-Garcia
(74) *Attorney, Agent, or Firm*—Pepper Hamilton LLP

(57) ABSTRACT

The present invention concerns processes for the production and purification of compounds of the formula:

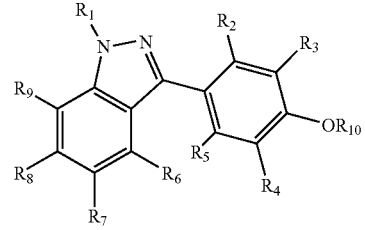

where $R_1$-$R_{10}$ are as defined in the specification. Preferred processes of the invention utilize a lithium bis(trimethylsilyl) amide, lithium dicyclohexylamide, or potassium bis(trimethylsilyl)amide base and a $R_1$—X alkylating agent where X is as described in the specification. An alcohol preferably is added to the product solution is used to promote crystallization of the desired product.

21 Claims, No Drawings

OTHER PUBLICATIONS

Bach, J. et al., "N-Acyl-5,5-dimethyl-oxazolidin-2-ones as latent aldehyde equivalents," *Tetrahedron Letters*, 1999, 40(36), 6677-6680.

Baldwin, J. et al., "Novel C-4 heteroaromatic kainoid analogues: a parallel synthesis approach," *Bioorganic & Medicinal Chemistry Letters*, 2000, 10(3), 309-311.

Baldwin, J. et al., "Parallel synthesis of novel heteroaromatic acromelic acid analogues from kainic acid," *Journal of Organic Chemistry*, 2001, 66(8), 2588-2596.

Baldwin, J. et al., "Enzymatic Synthesis of Bicyclic γ-Lactams using Clavaminic Acid Synthase," *Journal of the Chemical Society, Chemical Communications*, 1992, (12), 877-879.

Banfi, L. et al., "Synthesis of a methoxy-substituted lactenediyne," *Tetrahedron Letters*, 2000, 41(33), 6523-6526.

Barrett, A. et al., "Tandem ireland-claisen rearrangement ring-closing alkene metathesis in the construction of bicyclic beta-lactam carboxylic esters," *Journal of Organic Chemistry*, 2000, 65(12), 3716-3721.

Battistini, L. et al., "Diastereoselective synthesis of a novel lactam peptidomimetic exploiting vinylogous Mannich addition of 2-silyloxyfuran reagents," *Tetrahedron: Asymmetry*, 1999, 10(4), 765-773.

Bernardo, P. et al., "A simple and concise route to calothrixin B," *Tetrahedron Letters*, 2002, 43(16), 2939-2940.

Berry, J. et al., "5-Nitrofuran-2-ylmethyl group as a potential bioreductively activated pro-drug system," *Journal of the Chemical Society, Perkin Transactions 1: Organic and Bio-Organic Chemistry*, 1997, (8), 1147-1156.

Beyersbergen van Henegouwen, W. et al., "First Total Synthesis of ent-Gelsedine via a Novel Iodide-Promoted Allene N-Acyliminium Ion Cyclization," *Journal of Organic Chemistry*, 2000, 65(24), 8317-8325.

Bianco, A. et al., "Multistep synthesis of 2,5-diketopiperazines on different solid supports monitored by high resolution magic angle spinning NMR spectroscopy," *Journal of Combinatorial Chemistry*, 2000, 2(6), 681-690.

Bianco, A. et al., "Solid-phase synthesis and structural characterization of highly substituted hydroxyproline-based 2,5-diketopiperazines," *Journal of Organic Chemistry*, 2000, 65(7), 2179-2187.

Boa, A. et al., "Synthesis of α-Alkyl- α-Benzyl Amino Acid Derivatives, via the Diastereoselective Alkylation of (3S,5R)-N,3-Dibenzyl-3,4,5,6-tetrahydro-5-phenyl-1,4-oxazin-2-one," *Journal of the Chemical Society, Perkin Transactions 1: Organic and Bio-Organic Chemistry*, 1993, (1972-1999) (4), 477-481.

Borthwick, A. et al., "Design and synthesis of pyrrolidine-5,5-transslactams (5-oxo-hexahydro-pyrrolo[3,2-b]pyrroles) as novel mechanism-based inhibitors of human cytomegalovirus protease. 1. The alpha-methyl-trans-lactam template," *Journal of Medicinal Chemistry*, 2000, 43(23), 4452-4464.

Brana, M. et al., "Synthesis of a New Bicyclic Tetrahydropyridine System Related to Enediyne Antibiotics," *Tetrahedron Letters*, 1994, 35(46), 8655-8.

Brands, K. et al., "Synthesis of an Optically Active Tricyclic Intermediate For Manzamines," *Hetrocycles*, 1990, 30(1, Spec. Issue), 257-261.

Brill, W. et al., "Synthesis of Nucleoside Methylphosphonothioates," *Tetrahedron Letters*, 1987, 28(28), 3205-3208.

Brown, G. et al., "The azomethine ylide strategy for β-lactam synthesis. An evaluation of alternative pathways for azomethine ylide generation," *Journal of the Chemical Society*, Perkin Transactions, 2001, 1(11), 1281-1289.

Bull, S. et al., "A chiral relay auxiliary for the synthesis of homochiral α-amino acids," *Journal of the Chemical Society, Perkin Transactions 1: Organic and Bio-Organic Chemistry*, 1998, (15) 2321-2330.

Burgaud, B. et al., "The Asymmetric Synthesis of Non-peptide CCK-A Receptor Agonists," *Tetrahedron: Asymmetry*, 1995, 6(5), 1081-1084.

Campbell, A. et al., "The stereoselective preparation of substituted pyrrolidines using titanium- and zirconium-mediated diene metallabicyclisation methodology: the total synthesis of ( . )-α-kainic acid," *Perkin*, 2000, 1(19), 3194-3204.

Cardillo, G. et al., "A Practical Method for the Synthesis of β-Amino α-Hydroxy Acids. Synthesis of Enantiomerically Pure Hydoxyaspartic Acid and Isoserine," *Synlett*, 1999, (11), 1727-1730.

Cardona, F. et al., "Synthesis of (z)-3-Deoxy-3-(1,2,3,6-tetradeoxy-3,6-imino-L-arabino-Hexitol-1-C-ylidene)-D-xylo-Hexose Derivatives. First Examples of Homo-(1→3)-C-Linked Iminodisaccharides," *Journal of Carbohydrate Chemistry*, 2000, 19(4 & 5), 555-571.

Carland, M. et al., "Nucleophilic and radical chemistry of benzylselenides: preparation of novel selenocephems and selenopenams," *Tetrahedron Letters*, 2001, 42(28), 4737-4739.

Carretero, J. et al., "Stereoselective Synthesis of Polyhydroxylated Indolizidines from γ-Hydroxy α,β-Unsaturated Sulfones," *Journal of Organic Chemistry*, 1998, 63(9), 2993-3005.

Cases, M. et al., "Total Synthesis of the Furanocembrane bis-Deoxylophotoxin," *Synlett*, 2001, (12), 1869-1872.

Chung, S. et al., "Design and Synthetic Studies of Geometric Analogues of Quinolone Carboxylate Antibacterials," *Korean Journal of Medicinal Chemistry*, 1996, 6(1), 22-34.

Comins, D. et al., "Photochemical reactions of chiral 2,3-dihydro-4-pyridones: asymmetric synthesis of ( . )-perhydrohistrionicotoxin," *Chemical Communications*, 1998, (22), 2509-2510.

Comins, D. et al., "Enantiopure N-Acyldihydropyridones as Synthetic Intermediates: Asymmetric Synthesis of Benzomorphans," *Organic Letters*, 1999, 1(4), 657-659.

Confalone, P. et al., "Design and Synthesis of Potential DNA Cross-Linking Reagents Based on the Anthramycin Class of Minor Groove Binding Compounds," *Organic Chemistry*, 1998, 53(3), 482-487.

Craven, A. et al., "Cytochalasan Synthesis. Synthesis of (17S, 18S)-17, 18-Dihydroxy-10-(prop-2-yl)-14-methyl-[11]Cytochalasa-6(7), $13^Z$, $19^E$-triene-1,21-dione, an Isomer of Aspochalasin C," *Tetrahedron*, 1989, 45(8), 2417-2429.

Davies, S. et al., "Asymmetric syntheses of moiramide B and andrimid," *Journal of the Chemical Society, Perkin Transactions 1: Organic and Bio-Organic Chemistry*, 1998, (17), 2635-2644.

Davies, S. et al., "Bifunctional Chiral Auxiliaries 8: Utilisation of Tartaric Acid Derived Auxiliaries in Aldol and Alkylation Reactions," *Tetrahedron*, 1994, 50(25), 7521-7534.

Davis, F. et al., "Asymmetric Synthesis of α-Hydroxy Carboxylic Acids: Direct Oxidation of Chiral Amide Enolates Using 2-Sulfonyloxaziridines," *Tetrahedron Letters*, 1985, 26(30), 3539-3542.

Dellaria, J. et al., "Enantioselective Synthesis of α-Amino Acid Derivatives via the Stereoselective Alkylation of a Homochiral Glycine Enolate Synthon," *Journal of Organic Chemistry*, 1989, 54(16), 3916-3926.

Deziel, R. et al., "Synthesis of 1-8-methylcarbapenem key intermediates involving the labile acyl auxiliary 4,4-dimethyl-1,3-oxazolidine-2-thione," *Tetrahedron Letters*, 1989, 30(11), 1345-1348.

Dixon, D. et al., "Asymmetric synthesis of moiramide B," *Chemical Communications* (Cambridge), 1996, (15), 1797-1798.

Dockner, M. et al., "Enantiopure Indolizidones and Pyrrolizidones from Maleic Imide," *Bulletin des Societes Chimiques Belges*, 1994, 103(7-8), 379-87.

Dominguez, E. et al., "Efficient synthesis of 4,4-disubstituted-3,4-dihydro-1H-2,1,3-benzothiadiazine 2,2-dioxides," *Tetrahedron Letters*, 2000, 41(50), 9825-9828.

Dyke, H. et al., "Cytochalasan Synthesis: Total Synthesis of Cytochalasin G," *Journal of the Chemical Society, Perkin Transactions 1: Organic and Bio-Organic Chemistry*, 1989, (1972-1999) (3), 525-528.

Ekhato, I. et al., "Tetrahydro-pyrrolo-[2,3-b]indole-1,2,8-tricarboxylic Acid Ester in the Enantiospecific Preparation of ά-Methyltryptophan: Application in the Preparation of Carbon-14 Labeled PD 145942 and PD 154075," *Journal of Labelled Compounds & Radiopharmaceuticals*, 1997, 39(12), 1019-1038.

Ernst, M. et al., "A Novel Route to Iridoids: Enantioselective Syntheses of Isoiridomyrmecin and ά-Skytanthine," *Synthesis*, 2002, (14), 1953-1955.

Estiarte, M. et al., "Synthesis of a 3-aminopiperidin-2,5-dione as a conformationally constrained surrogate of the Ala-Gly dipeptide," *Tetrahedron*, 2001, 57(1), 157-161.

Feldman, K. et al., "Alkynyliodonium Salts in Organic Synthesis. Application to the Total Synthesis of (−)-Agelastatin A and (−)-Agelastatin B," *Journal of the American Chemical Society*, 2002, 124(31), 9060-9061.

Feldman, K. et al., "Diazonamide Synthesis Studies: Use of Negishi Coupling to Fashion Diazonamide-Related Biaryls with Defined Axial Chirality," *Organic Letters*, 2002, 4(20), 3525-3528.

Ferrer, S. et al., "N-and O-Alkylation of isoquinolin-1-ones in the Mitsunobu reaction; development of potential drug delivery systems," *Journal of the Chemical Society*, Perkin Transactions 2002, 1(3), 335-340.

Ferrer, S. et al., "Studies on the reductively triggered release of heterocyclic and steroid drugs from 5-nitrothien-2-ylmethyl prodrugs," *Tetrahedron*, 2003, 59(19), 3437-3444.

Frederick, M. et al., "A Copper-Catalyzed C-N Bond Formation involving sp-Hybridized Carbons. A Direct Entry to Chiral Ynamides via N-Alkynylation of Amides," *Journal of the American Chemical Society*, 2003, 125(9), 2368-2369.

Frutos, R. et al., "An improved synthesis of N-aryl-hydantoin LFA-1 antagonists via the enantiospecific alkylation of an isobutyraldehyde-derived imidazolidinone template," *Tetrahedron: Asymmetry*, 2001, 12(1), 101-104.

Fujimura, Y. et al., "Reaction of 2-Bromo-2,3-Dihydro-1H-Pyrazolo [1, 2-a]Indazolium Bromides with Alkaline Solution," *Heterocycles*, 1986, 24(10), 2771-2775.

Gerard, S. et al., "Synthesis, hydrolysis, biochemical and theoretical evaluation of 1,4-bis(alkoxycarbonyl) azetidin-2-ones as potential elastase inhibitors," *Tetrahedron*, 2002, 58(12), 2423-2433.

Giacobbe, S. et al., "Synthesis of Substituted Indole-2-Carboxylates: Versatile Introduction of a Carbamoyl Moiety at the C-3 Position," *Synthetic Communications*, 1999, 29(18), 3125-3135.

Girard, S. et al., "A short and efficient synthesis of unnatural (R)-nicotine," *Tetrahedron Letters*, 2000, 41(48), 9245-9249.

Guillena, G. et al., "1,5-Dimethyl-4-phenylimidazolidin-2-one-Derived Iminic Glycinimides: Useful New Reagents for Practical Asymmetric Synthesis of α-Amino Acids," *Journal of Organic Chemistry*, 2000, 65(22), 7310-7322.

Guillena, G. et al., "(4R,5S)-1,5-Dimethyl-4-phenylimidazolidin-2-one as a chiral auxiliary for the diastereoselective alkylation of a new iminic glycine derivative: practical asymmetric synthesis of α-amino acids," *Tetrahedron: Asymmetry*, 1998, 9(7), 1125-1129.

Hanessian, S. et al., "A Novel Ring-Closure Strategy for the Carbapenems: The Total Synthesis of (+)-Thienamycin," *Journal of Organic Chemistry*, 1990, 55(10), 3098-3103.

Hanessian, S. et al., "Probing the functional requirements of the L-haba side-chain of amikacin-synthesis, 16S A-site rRNA binding, and antibacterial activity," *Tetrahedron*, 2003, 59(7), 995-1007.

Harkin, S. et al., "Cytochalasan Synthesis: Macrocycle Synthesis Using Intramolecular Diels-Alder Reactions. X-Ray Crystal Structure of 10-Phenyl[ll]cytochalasa-6(7),13′-diene-1,21-dione," *Journal of the Chemical Society, Perkin Transactions 1: Organic and Bio-Organic Chemistry*, 1989, (1972-1999) (3), 489-497.

Herdeis, C. et al., "A stereoselective synthesis of 3-substituted (S)-pyroglutamic and glutamic acids via OBO ester derivatives," *Tetrahedron*, 2003, 59(2), 217-229.

Hoarau, S. et al., "Synthesis of Enantiomerically Pure (2R, 5S)-and (2R,5R)-5-Hydroxypipecolic Acid from Glycinate Schiff Bases," *Tetrahedron: Asymmetry*, 1996, 7(9), 2585-2593.

Hoshimoto, S. et al., "Sterically Constrained 'Roofed' 2-Thiazolidinones as Excellent Chiral Auxiliaries," *Chemical & Pharmaceutical Bulletin*, 2000, 48(10), 1541-1544.

Hu, H. et al., "Two Efficient Syntheses of (±)-anti-N-Benzyl-3-Amino-4-Hydroxyhexahydroazepine 1,2," *Tetrahedron Letters*, 1995, 36(21), 3659-3662.

Humphrey, J. et al., "Enantioselective Total Syntheses of Manzamine A and related Alkaloids,"*Journal of the American Chemical Society*, 2002, 124(29), 8584-8592.

Hyo, M. et al., "Synthesis of 2-Cyano-1-oxocarbapenam-3-carboxylate," *Bulletin of the Korean Chemical Society*, 1995, 16(8), 687-688.

Iimura, S. et al., "Orally Active Docetaxel Analogue: Synthesis of 10-Deoxy-10-C-morpholinoethyl Docetaxel Analogues," *Bioorganic & Chemistry Letters*, 2001, 11(3), 407-410.

Ishida, Y. et al., "Homochiral Supramolecular Polymerization of an "S"-Shaped Chiral Monomer: Translation of Optical Purity into Molecular Weight Distribution," *Journal of the American Chemical Society*, 2002, 124(47), 14017-14019.

Kanazawa, A. et al., "Highly Stereocontrolled and Efficient Preparation of the Protected, Esterification-Ready Docetaxel (Taxotere) Side Chain," *Journal of Organic Chemistry*, 1994, 59(6), 1238-1240.

Kanazawa, A. et al., "Direct, Stereoselective Synthesis of the Protected Paclitaxel (Taxol) Side Chain and High-yield transformation to Paclitaxel," *Journal of the Chemical Society, Chemical Communications*, 1994, (22), 2591-2.

Kant, J. et al., "Diastereoselective Addition of Grignard Reagents to Azetidine-2,3-dione: Synthesis of Novel Taxol® Analogues," *Tetrahedron Letters*, 1996, 37(36), 6495-6498.

Karimi, F. et al., "Synthesis of $^{11}$C-amides using [$^{11}$C]carbon monoxide and in situ activated amines by palladium-mediated carboxaminations," *Organic & Biomolecular Chemistry*, 2003, 1(3), 541-546.

Kende, A. et al., "Enantioselective Total Synthesis of Lankacidin C," *Journal of the American Chemical Society*, 1993, 115(21), 9842-9843.

Kende, A. et al., "Total Synthesis of the Macrolide Antitumor Antibiotic Lankacidin C," *Journal of the American Chemical Society*, 1995, 117(31), 8258-8270.

Kobayashi, S. et al., "Catalytic Asymmetric Synthesis of Febrifugine and Isofebrifugine," *Tetrahedron Letters*, 1999, 40(11), 2175-2178.

Lauffer, D. et al., "A Practical Synthesis of (S) 3-tert-Butoxycarbonylamino-2-oxo-2,3,4,5-tetrahydro-1,5-benzodiazepine-1-acetic Acid Methyl Ester as of Conformationally Restricted Dipeptido-Mimetic for Caspase-1 (ICE) Inhibitors," *Bioorganic & Medicinal Chemistry Letters*, 2002, 12(8), 1225-1227.

Lerchner, A. et al., "First Total Synthesis of (±)-Strychnofoline via a Highly Selective Ring-Expansion Reaction," *Journal of the American Chemical Society*, 2002, 124(50), 14826-14827.

Li, H. et al., "A Convenient N-Protection of Pyroglutamate Derivatives," *Synthetic Communications*, 1995, 25(24), 4045-4052.

Lin, J. et al., "Asymmetric Alkylation Mediated by Tricyclic Chiral Sultam Auxiliaries," *Tetrahedron*, 1999, 55(49), 13983-13998.

MacDonald, S. et al., "A Flexible, Practical, and Stereoselective Synthesis of Enantiomerically Pure trans-5-Oxohexahydropyrrolo[3,2-b]pyrroles (Pyrrolidine-trans-lactams), a New Class of Serine Protease Inhibitors, Using Acyliminium Methodology," *Journal of Organic Chemistry*, 1999, 64(14), 5166-5175.

MacDonald, S. et al., "Syntheses of templates derived from pyrrolidine trans-lactams as potential serine protease inhibitors," *Tetrahedron Letters*, 2002, 43(29), 5057-5060.

Magnus, P. et al., "Studies on the Synthesis of the Antitumor Agent CC-1065. Synthesis of the Unprotected Cyclopropapyrroloindole A Portion Using the 3,3'-Bipyrrole Strategy," *Journal of the American Chemical Society*, 1987, 109(9), 2706-2711.

Marchand-Brynaert, J. et al., "Bicyclic Imidazolidinones as Potential Antibiotics," *Bulletin des Societes Chimiques Belges*, 1988, 97(11-12), 1081-1093.

Meyers, C. et al., "Total Synthesis of (−)-Spirotryprostatin B," *Angewandte Chemie*, International Edition, 2003, 42(6), 694-696.

Murray, P. et al., "The Enantiospecific Synthesis of Functionalised Pipecolic Acids as Constrained Analogues of Lysine," *Tetrahedron Letters*, 1996, 37(11), 1875-1878.

Myers, A. et al., "Asymmetric Synthesis of Chiral Organofluorine Compounds: Use of Nonracemic Fluoroiodoacetic Acid as a Practical Electrophile and its Application to the Synthesis of Monofluoro Hydroxyethylene Dipeptide Isosteres within a Novel Series of HIV Protease Inhibitors," *Journal of the American Chemical Society*, 2001, 123(30), 7207-7219.

Nagasaka, T. et al., "Stereoselective Formal Synthesis of (±)-Monomorine I From 6-Methyl-2-Piperidinone," *Heterocycles*, 1990, 30(1, Spec. Issue), 561-566.

Nagasaka, T. et al., "Stereoselective Synthesis of Tilivalline," *Journal of Organic Chemistry*, 1998, 63(20), 6797-6801.

Nagasaka, T. et al., "Stereoselective Synthesis of Tilivalline," *Tetrahedron Letters*, 1989, 14(4), 1871-1872.

Newlander, K. et al., "A Novel Constrained Reduced-Amide Inhibitor of HIV-1 Protease Derived from the Sequential Incorporation of γ-Turn Mimetics into a Model Substrate," *Journal of Medicinal Chemistry*, 1993, 36(16), 2321-31.

Nicolaou, K. et al., "Model Studies towards Diazonamide A: Synthesis of the Heterocyclic Core," *Angewandte Chemie*, International Edition, 2000, 39(19), 3473-3478.

Nomoto, T. et al., "A New Route to 1,3-Dienes using 3-Methylene-2,3-dihydrothiophene *S,S*-Dioxide as an Allyl Sulphone and Michael Acceptor: Synthesis of (±)-Ipsenol," *Journal of the Chemical Society, Chemical Communications*, 1989, (5), 295-297.

Oda, K. et al., "An efficient route to chiral, non-racemic 3-alkyl-3-arylpyrrolidines. Improved stereoselectivity in alkylation of bicyclic lactams and the effect of leaving groups," *Tetrahedron Letters*, 2000, 41(43), 8193-8197.

Orena, M. et al., "A New Approach to 2-Phenylthioalcohols in High Optical Purity," *Tetrahedron Letters*, 1992, 33(26), 3797-3800.

Overman, L. et al., "Enantioselective Total Synthesis of the Cyclotryptamine Alkaloid Idiospermuline," *Angewandte Chemie*, International Edition, 2003, 42(22), 2525-2528.

Ozawa, T. et al., "Total Synthesis of the Marine Alkaloids (−)-Lepadins A, B, and C Based on Stereocontrolled Intramolecular Acylnitroso-Diels-Alder Reaction," *Journal of Organic Chemistry*, 2001, 66(10), 3338-3347.

Ozawa, T. et al., "Total Synthesis of the Marine Alkaloid (−)-Lepadin B," *Organic Letters*, 2000, 2(19), 2955-2958.

Polt, R. et al., "Stereoselective Alkylation of Glycine Units in Dipeptide Derivatives: "Chirality Transfer" via a Pivalaldehyde *N,N*-Acetal Center," *Journal of the American Chemical Society*, 1989, 111(7), 2622-2632.

Reyes, A. et al., "Stereoselective Tandem Michael-Intramolecular Cyclization Approach to Functionalized Pyrroloisoindolones," *Tetrahedron*, 1999, 55(37), 11187-11202.

Robiette, R. et al., "A Study of the Alkylation and Rearrangement Products of Chiral 1,3-Oxazolidine- and Thiazolidine-2-Thiones," *Heterocycles*, 2003, 60(3), 523-536.

Robl, J. et al., "A Synthetic Route for the Generation of C-7 Substituted Azepinones," *Tetrahedron Letters*, 1994, 35(9), 1393-1396.

Roland, S. et al., "π-Allyl Palladium Ring Closure Strategy for the Synthesis of a 1β-Methylcarbapenem Intermediate," *Tetrahedron Letters*, 1995, 36(17), 3007-3010.

Sato, T. et al., "Synthesis of 7-Azabicyclo[2.2.1]Heptane and 8-Azabicyclo[3.2.1]Octane Systems Using Radical Cyclization," *Heterocycles*, 1994, 37(1), 245-248.

Sherrill, R. et al., "1,4-Benzodiazepine Peripheral Cholecystokinin (CCK-A) Receptor Agonists," *Bioorganic & Medicinal Chemistry Letters*, 2001, 11(9), 1145-1148.

Siddiqui, M. et al., "Synthesis of Constrained Bicyclic Dipeptide Mimetics," *Tetrahedron Letters*, 1997, 38(51), 8807-8810.

Smith III, A. et al., "Total Synthesis of (+)-Calyculin A and (−)-Calyculin B: Cyanotetraene Construction, Asymmetric Synthesis of the C(26-37) Oxazole, Fragment Assembly, and Final Elaboration," *Journal of the American Chemical Society*, 1999, 121(45), 10478-10486.

Smith III, A. et al., "Total Synthesis of (+)-Phyllanthocin," *Journal of the American Chemical Society*, 1987, 109(4), 1269-1272.

Soll, R. et al., "The Synthesis and pharmacological evaluation of indole congeners of the calcium entry blocker verapamil," *European Journal of Medicinal Chemistry*, 1990, 25(2), 191-196.

Soucy, F. et al., "A Novel and Efficient Synthesis of a Highly Active Analogue of *clasto*-Lactacystin β-Lactone," *Journal of the American Chemical Society*, 1999, 121(43), 9967-9976.

Sugahara, T. et al., "Asymmetric Total Syntheses of (+)- and (−)-Pulo'Upone," *Tetrahedron Letters*, 1989, 30(14), 1821-1824.

Takadoi, M. et al., "Synthetic studies of himbacine, a potent antagonist of the muscarini $M_2$ subtype receptor 1. Stereoselective total synthesis and antagonistic activity of enantiomeric pairs of himbacine and (2'S,6'R)-diepihimbacine, 4-epihimbacine, and novel himbacine congeners," *Tetrahedron*, 2002, 58(50), 9903-9923.

Takahashi, Y. et al., "Synthetic Study of *cis*-3-Amino-4-(1-hydroxyalkyl)azetidin-2-ones Using L-Aspartic Acid as a Chiral Synthon," *Chemical & Pharmaceutical Bulletin*, 1986, 34(7), 2732-2742.

Taylor, G. et al., "On the Ritter Reaction of Cyclic Hydroxyamines: Synthesis of Conformationally-Restricted Reduced Amide Dipeptide Isosteres," *Tetrahedron Letters*, 1996, 37(8), 1297-1300.

Vourloumis, D. et al., "Novel 2,5-Dideoxystreptamine Derivatives Targeting the Ribosomal Decoding Site RNA," *Bioorganic & Medicinal Chemistry Letters*, 2002, 12(23), 3367-3372.

Wasserman, H. et al., "Penem Synthesis through $C_3$-N Ring Closure of a β-Lactam Precursor," *Journal of the American Chemical Society*, 1985, 107(5), 1444-1446.

Wee, A. et al., "A Dirhodium(II)-Carbenoid Route to (−)- and (+)-Geissman-Waiss Lactone: Synthesis of (1R,7R,8R)-(−)-Turneforcidine," *Journal of Organic Chemistry*, 2001, 66(25), 8513-8517.

Wild, H. et al., "First Synthetic Access to 6-(Methylene)oxapenems: A New Class of β-Lactamase Inhibitors," *Synthesis*, 1992, (11), 1099-1103.

Wrobel, J. et al., "Conformationally Rigid Analogues of Aldose Reductase Inhibitor, Tolrestat. Novel Syntheses of Naphthalene-Fused γ-, δ-, and ε-Lactams," *Journal of Organic Chemistry*, 1990, 55(9), 2694-2702.

You, J. et al., "Studies on the Synthesis of 1-Hydroxycarbapenems," *Journal of the Korean Chemical Society*, 1998, 42(1), 69-77.

Zhang, X. et al., "Design and synthesis of 6-amino-5-oxo-1,2,3,5-tetrahydro-3-indolizinecarboxylic acids as β-sheet peptidomimetics," *Tetrahedron Letters*, 2002, 43(52), 9663-9666.

Zibuck, R. et al., "Total Synthesis of (+)-Latrunculin B," *Journal of the American Chemical Society*, 1986, 108(9), 2451-2453.

\* cited by examiner

PREPARATION AND PURIFICATION OF 4-(INDAZOL-3-YL)PHENOLS

RELATED APPLICATIONS

This application claims the benefit of U.S. Provisional Application No. 60/622,240, filed on Oct. 26, 2004, the disclosure of which is incorporated herein by reference in its entirety.

FIELD OF THE INVENTION

This invention relates, in part, to preparation and purification of 4-(indazol-3-yl)phenols.

BACKGROUND OF THE INVENTION 4-(Indazol-3-yl)phenols such as 4-(1-allyl-1H-indazol-3-yl)-benzene-1,3-diols have been indicated for use in the treatment of the inflammatory component of diseases such as atherosclerosis, myocardial infarction, congestive heart failure, inflammatory bowel disease, arthritis, type II diabetes, and autoimmune diseases such as multiple sclerosis and rheumatoid arthritis. Intermediates in the production of 4-(1-allyl-1H-indazol-3-yl)-benzene-1,3-diols include their 1,3-dimethoxy analogs, although many known synthetic methods for such intermediates produce mixtures of 1-allyl-3-(2,4-dimethoxyphenyl)-7-trifluoromethyl-1H-indazole and 2-allyl-3-(2,4-dimethoxyphenyl)-7-trifluoromethyl-1H-indazole isomers. Because the two isomers are produced in roughly equal proportions, such mixtures typically are purified using silica gel chromatography. Such chromatographic purification, however, is time-consuming and costly when carried out on a large scale. A more economical method for the production of 4-(indazole-3-yl)phenols is desirable.

SUMMARY OF THE INVENTION

In one aspect, the present invention relates to 4-(indazol-3-yl)phenols and their ether analogs, as well as methods for their preparation. Of particular interest are 4-(1-allyl-1H-indazol-3-yl)-benzene-1,3-diols.

In certain embodiments, the methods of the invention comprise the steps of:
contacting a compound of the formula:

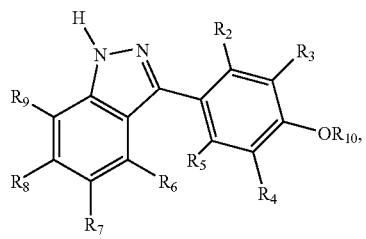

wherein:
$R_2$, $R_3$, $R_4$, and $R_5$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CN, —NO$_2$, —CHO, or —CO$_2R_{11}$;
$R_6$, $R_7$, $R_8$, and $R_9$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CO$_2R_{11}$, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S;
$R_{10}$ is hydrogen, alkyl of 1-6 carbon atoms, —CO$_2R_{11}$, —CONHR$_{11}$, —P(=O)(OH)OR$_{11}$, —CO(CH$_2$)$_n$CH(NHR$_{12}$)CO$_2$R, or a hydroxyl protecting group;
$R_{11}$, is hydrogen, alkyl of 1-6 carbon atoms, aryl of 6-20 carbon atoms, or arylalkyl of 7-26 carbon atoms;
$R_{12}$ is hydrogen or —CO$_2R_{11}$; and
n=0-3;

with lithium bis(trimethylsilyl)amide, lithium dicyclohexylamide, or potassium bis(trimethylsilyl)amide in the presence of a dipolar aprotic solvent to produce a first reaction mixture;
contacting the first reaction mixture with a compound of the formula R$_1$—X, where:
$R_1$ is alkyl of 1-6 carbon atoms, alkenyl of 2-7 carbon atoms, cycloalkyl of 3-8 carbon atoms, cycloalkenyl of 4-8 carbon atoms, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S; and
X is leaving group;

to produce a second reaction mixture;
mixing the second reaction mixture with an alcohol;
optionally cooling the second reaction mixture;
producing a precipitate comprising a compound of the formula:

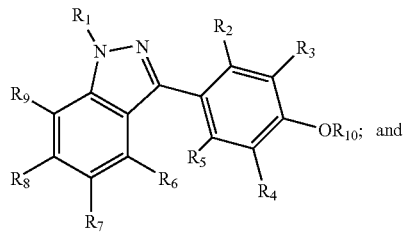

isolating the precipitate.

In some embodiments, the alcohol is methanol, ethanol, 1-propanol, 2-propanol, or mixtures thereof. X may be Cl, Br, or I in some embodiments.

In certain embodiments, the solvent comprises tetrahydrofuran. In other embodiments, the solvent further comprises a second component that is dimethylformamide (DMF), hexamethyphosphoramide (HMPA), N,N'-dimethyl-N,N'-propylene urea (DMPU), or 2,2,6,6-tetramethylpiperidine (TMP). In some embodiments, the second component is preferably DMF.

Cooling of the second reaction mixture is optional. A precipitate may form without such cooling. Cooling is preferred, however, in certain embodiments to assist in producing the precipitate. In certain embodiments, the mixture is cooled to about 22° C. or below. In other embodiments, the mixture is cooled to about 20° C. or below. In other embodiments, the second reaction mixture can be cooled to a temperature of about 10° C. or below to produce the precipitate. In certain embodiments, at least a portion of the solvent (e.g., at least one half of the solvent by weight) is removed prior to cooling the second reaction mixture to produce the precipitate.

Preferred processes further comprise washing the precipitate with ethanol at a temperature of about 10° C. or below and then drying the washed precipitate.

In some preferred embodiments, the process further comprises converting $R_2$ to OH and $R_{10}$ to H to produce a compound of the formula:

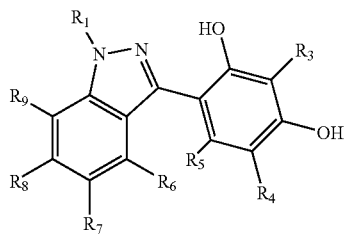

where $R_1$ and $R_3$-$R_9$ are as defined herein.

In certain of these embodiments, the conversion is accomplished by base hydrolysis, acid hydrolysis, or hydrogenation.

The present invention also provides the products produced by the processes of the instant invention.

DETAILED DESCRIPTION OF ILLUSTRATIVE EMBODIMENTS

The instant invention concerns production and purification of 4-(indazol-3-yl)phenol and 4(indazol-3-yl)alkoxyphenyl compounds. In preferred embodiments, the invention concerns compounds of the formula:

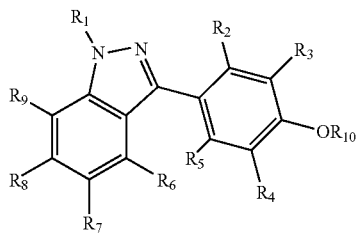

wherein $R_1$ is alkyl of 1-6 carbon atoms, alkenyl of 2-7 carbon atoms, cycloalkyl of 3-8 carbon atoms, cycloalkenyl of 4-8 carbon atoms, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S;

$R_2$, $R_3$, $R_4$, and $R_5$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CN, —$NO_2$, —CHO, or —$CO_2R_{11}$;

$R_6$, $R_7$, $R_8$, and $R_9$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —$CO_2R_{11}$, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S;

$R_{10}$ is hydrogen, alkyl of 1-6 carbon atoms, —$CO_2R_{11}$, —$CONHR_{11}$, —P(=O)(OH)$OR_{11}$, or —CO($CH_2$)$_n$CH(NHR$_{12}$)$CO_2$R;

$R_{11}$, is hydrogen, alkyl of 1-6 carbon atoms, aryl of 6-20 carbon atoms, or arylalkyl of 7-26 carbon atoms;

$R_{12}$ is hydrogen or —$CO_2R_{11}$; and n=0-3.

"Alkyl," as used herein, refers to an aliphatic hydrocarbon chain having one to six, preferably one to four, and more preferably one to three carbon atoms, and includes, but is not limited to, straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. The term "alkyl" further includes both unsubstituted and mono-, di- and tri-substituted hydrocarbon groups. In some embodiments, substitution with halogen substituents is preferred.

The term "alkenyl" refers to an unsaturated or partially unsaturated aliphatic hydrocarbon group having the specified number of carbon atoms, for example ethenyl, 1-propenyl, 2, butenyl, etc. The term "alkenyl" further includes both unsubstituted and mono-, di- and tri-substituted hydrocarbon groups, with halogen substitution particularly preferred. In some embodiments, the alkenyl group has 2-7 carbon atoms.

The term "cycloalkyl" includes cyclized alkyl chains having the specified number of carbon atoms, e.g., cyclopropyl, cyclobutyl, cyclopentyl, and cyclohexyl. In some embodiments, the cylcoalkyl has 3-8 carbon atoms.

The term "cycloalkenyl" includes cyclized alkyl chains containing an alkenyl group having the specified number of carbon atoms, e.g., cyclopentenyl, cyclohexenyl, etc. In some embodiments, the cylcoalkenyl has 4-8 carbon atoms.

The term "halogen" includes fluorine, chlorine, iodine, and bromine.

The term "aryl" means an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Some aryl groups have 6 to 20 carbon atoms. Examples of aryl moieties include, but are not limited to, chemical groups such as phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. Groups containing aryl or heteroaryl moieties may optionally be substituted with one to three substituents independently selected from halogen, alkyl, and alkoxy groups.

The term "arylalkyl" means aryl, as herein before defined, suitably substituted on any open ring position with an alkyl moiety wherein the alkyl chain is either a ($C_1$-$C_6$) straight or ($C_2$-$C_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "alkoxy," as used herein, refers to the group R—O— where R is an alkyl group as described herein.

The term "aryloxy," as used herein, refers to the group Ar—O—, where Ar is an aryl group as described herein.

The term "heterocyclic ring or ring system", employed alone or in combination with other terms, is defined herein as an unsaturated, partially unsaturated or saturated ring or ring system, which may be a single ring (monocyclic) or multiple rings (bicyclic, up to three rings) fused together or linked covalently. The rings may contain from one to four hetero atoms selected from nitrogen (N), oxygen (O), or sulfur (S), wherein the nitrogen or sulfur atom(s) are optionally oxidized, or the nitrogen atom(s) are optionally quarternized. Any suitable ring position of the heteroaryl moiety may be covalently linked to the defined chemical structure. Examples of unsaturated heterocyclic rings or ring systems include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like. Examples of saturated or partially unsaturated heterocyclic rings or ring systems include, but are not limited to, chemical groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

Representative substituents for alkyl, alkenyl, cycloalkyl, aryl, arylalkyl, alkoxy, aryloxy, or heterocyclic ring or ring systems, include —R', OR', =O, =NR', =N—OR', —NR'R'', —SR', halo, trifluoromethyl, trifluoromethoxy, —OC(O)R', —CO$_2$R', —C(O)NR'R'', —OC(O)NR'R'', —NR'C(O)R', —NR'CO$_2$R', —NR'C(O)NR'R'', —NH—C(NH$_2$)=NH, —NR'C(NH$_2$)=NH, —NH—C(NH$_2$)=NR', —S(O)R', —S(O)$_2$R', —S(O)$_2$NR'R'', cyano, and nitro; wherein, R' or R'' are each, independently, hydrogen, unsubstituted (C$_1$-C$_6$)alkyl, unsubstituted (C$_3$-C$_7$)cycloalkyl, aryl, aryl-(C$_1$-C$_3$)alkyl, aryloxy-(C$_1$-C$_3$)alkyl, arylthio-(C$_1$-C$_3$)alkyl, heteroaryl, heteroaryl-(C$_1$-C$_3$)alkyl, heteroaryloxy-(C$_1$-C$_3$)alkyl, or heteroarylthio-(C$_1$-C$_3$)alkyl groups; or if optionally taken together may be linked as an alkylene-group to form a ring.

The term "leaving group" represents a moiety that is attached to an electrophile and can be displaced by a nucleophile in a nucleophilic substitution reaction. Leaving groups are well known to those skilled in the art. See, for example, Jerry March, Advanced Organic Chemistry, 4th ed., John Wiley & Sons, New York, 1992. Leaving groups include halides, tosyl, and mesyl. Suitable halides include Br, Cl, and I.

Preferred compounds of this invention include those in which:
  R$_1$ is alkyl of 1-6 carbon atoms, alkenyl of 2-7 carbon atoms, cycloalkyl of 3-8 carbon atoms, cycloalkenyl of 4-8 carbon atoms, or a saturated, unsaturated, or partially unsaturated heterocyclic ring or ring system of 4-14 atoms, containing 1-4 heteroatoms selected from N, O, and S; and/or
  R$_2$ is hydrogen, alkyl of 1-6 carbon atoms, alkenyl of 2-7 carbon atoms, hydroxy, alkoxy of 1-6 carbon atoms, or halogen; and/or
  R$_7$ and R$_9$, are each, independently, hydrogen, alkyl of 1-6 carbon atoms, hydroxy, halogen, trifluoromethyl, —CO$_2$R$_{11}$, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S, where the remaining substituents are as defined above.

Preferred compounds of this invention also include those of in which:
  R$_1$ is alkyl of 1-6 carbon atoms, alkenyl of 2-7 carbon atoms, cycloalkyl of 3-8 carbon atoms, or cycloalkenyl of 4-8 carbon atoms; and/or
  R$_2$ is hydrogen, alkyl of 1-6 carbon atoms, halogen, or hydroxy; and/or
  R$_9$ is alkyl of 1-6 carbon atoms, halogen, trifluoromethyl, —CO$_2$R$_{11}$, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S; and/or
  R$_{10}$ is hydrogen, where the remaining substituents are as defined above.

Additional preferred compounds of this invention include those in which:
  R$_1$ is alkyl of 1-6 carbon atoms or alkenyl of 2-7 carbon atoms; and/or
  R$_9$ is alkyl of 1-6 carbon atoms, halogen, or trifluoromethyl, where the remaining substituents are as defined above.

In certain preferred embodiments, R$_1$ is allyl, R$_2$ is hydroxyl or alkoxy, R$_3$-R$_8$ are each H, R$_9$ is trifluoromethyl, and R$_{10}$ is H or alkyl.

The reagents used in the preparation of the compounds of this invention can be either commercially obtained or can be prepared by standard procedures described in the literature.

In certain embodiments, the starting material for the synthesis is a compound of the formula:

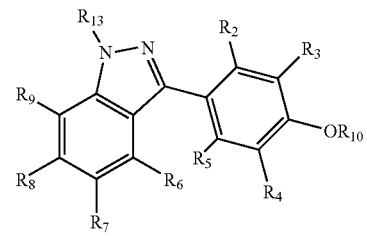

where R$_{13}$ is H and R$_2$-R$_{10}$ are as defined above. In some embodiments, R$_{10}$ is a hydroxyl protecting group. A protecting group is a moiety that renders a chemical functionality of a molecule inert to specific reaction conditions. The protecting group can later be removed from such functionality in a molecule, preferably without altering or substantially altering the remainder of the molecule. Protecting groups are well known in the art and are well described, for example, in Greene, T. W., et al., Protecting Groups in Organic Synthesis, 2nd edition, John Wiley and Sons, Inc., New York, (1991), the disclosure of which is incorporated herein by reference in its entirety. Such protecting groups include methyl, benzyloxymethyl, tert-butyl, benzyl and t-butyldiphenylsilyl.

A wide variety of techniques and reagents are available for the removal of hydroxyl protecting groups. Such techniques and agents are known to one skilled in the art. Hydroxyl protecting group can be removed, for example, by base hydrolysis, acid hydrolysis, or hydrogenation. In some embodiments, the conversion of $R_2$ to OH and $R_{10}$ to H is accomplished by acid hydrolysis in the presence of $BBr_3$ or a mixture of $BBr_3$ and $BCl_3$.

The starting material preferably is contacted with a base in the presence of a dipolar aprotic solvent to produce a first reaction mixture. This first reaction mixture is contacted with a compound of the formula $R_1$—X, where X is a leaving group, to produce a second reaction mixture. Ethanol is added to the second reaction mixture. The resulting solution is then cooled to a temperature of 20° C. or below to produce a precipitate. The precipitate can then be isolated by conventional means such as filtration.

Representative bases according to the present invention include lithium bis(trimethylsilyl)amide, lithium dicyclohexylamide, and lithium, sodium, or potassium bis(trimethylsilyl)amide. In some embodiments, reaction of the starting material with the base occurs at a reduced (below ambient) temperature. This reduced temperature can, for example, be −10° C. or below or −15° C. or below. The base may advantageously be added over a period of minutes or hours.

The first reaction mixture may be warmed to ambient temperature after the addition of the base. The addition of $R_1$—X may also be made over a period of minutes or hours. In some embodiments, the temperature is maintained at ambient or below. In other embodiments, the temperature is maintained at 15-20° C. After addition of $R_1$—X, the reaction mixture may optionally stirred for a period of time. In some embodiments, the period of time is several hours, 20 or more hours in certain embodiments, 40 or more hours in other embodiments. In certain embodiments, X is Cl, Br, or I. In some embodiments, that molar ratio of $R_1$—X to starting material is 1.0 or greater. In other embodiments, the ratio is greater than 1.0. In still other embodiments, the ratio is 1.1 or greater.

Preferred alcohol solvents are methanol, ethanol, 1-propanol, and 2-proponanol. In some embodiments, ethanol is preferred. In some embodiments, the ethanol used in the process is substantially anhydrous. Commercial anhydrous ethanol may contain an additional solvent as a denaturant. In some formulations, 0.5 to 0.6% (by weight) toluene or ethanol which is added as a denaturant. In some embodiments, this commercially available anhydrous ethanol is used in the instant processes.

In certain preferred methods, the ethanol containing solution is cooled to a temperature of 10° C. or below to produce the precipitate. This cooling can, for example, take place slowly over several minutes or hours. The solution may be cooled first to a temperature of 20° C. or less and then cooled to a second lower temperature of 10° C. or less. In certain embodiments, the first cooling stage takes from 1-10 hours, preferably from 2-4 hours. In certain embodiments, the second cooling stage takes from 1-10 hours, preferably from 0.5 to 2 hours. It generally is desirable to stir the solution for a period of time (1-3 hours in some embodiments) at the second temperature as the crystallization occurs.

In some embodiments, it is preferred that at least a portion of the solvent be removed prior to cooling the reaction mixture to produce the precipitate. In certain embodiments, it is preferred that at least 50% by volume of the solvent be removed prior to cooling the reaction mixture to produce the precipitate. The reduction in volume may be accomplished by distillation at atmospheric pressure. In other embodiments, reduced pressure may be used.

The dipolar aprotic solvent is selected so that the starting material, reaction intermediates, and reaction products are soluble in the solvent. The solvent should also be one that is substantially unreactive with the base employed. In some embodiments, the solvent is tetrahydrofuran (THF).

A second component can also be used in the solvent system. This component, can be for example, dimethylformamide (DMF), hexamethyphosphoramide (HMPA), N,N'-dimethyl-N,N'-propylene urea (DMPU), or 2,2,6,6-tetramethylpiperidine (TMP). In certain embodiments, the solvent comprises THF and at least one second component. Certain embodiments utilize a ratio of THF to second component of about 5 to about 12% based on weight of the THF and second component. In some embodiments, the molar ratio of second component to starting material is 1.0 or greater. In other embodiments, the ratio is 3.0 or greater. In still other embodiments, the ratio is 4.0 or greater.

After isolation of the precipitate, one may wash the precipitate with ethanol to help remove any impurities. In some embodiments, it is preferred that the washing use ethanol at a temperature of 10° C. or below. The washed precipitate may be dried by conventional techniques including applying heat and/or reduced pressure to the precipitate. In certain embodiments, the drying is accomplished at a temperature of 40-50° C. and at a pressure of ≦30 mm Hg.

The isolated precipitate may also be purified by other conventional methods such as recrystallization from a suitable solvent.

The instant invention is illustrated by the following reaction scheme using allyl bromide as an alkylating agent.

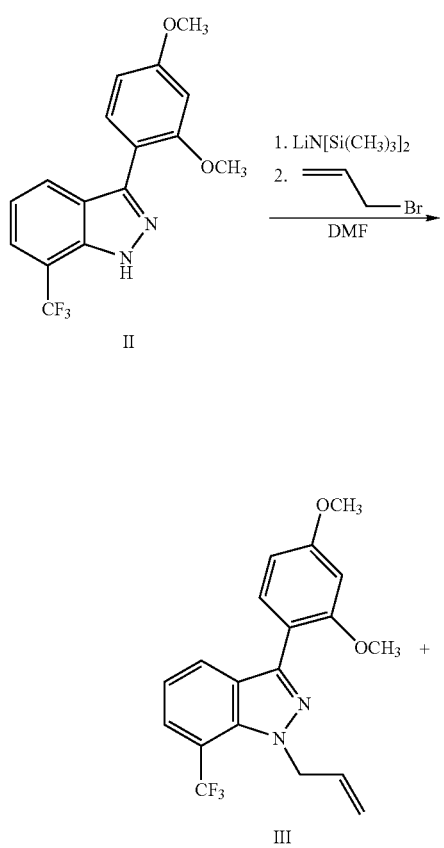

-continued

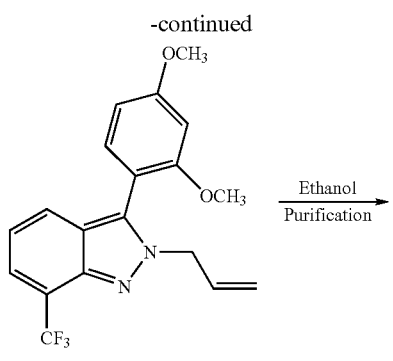
IV

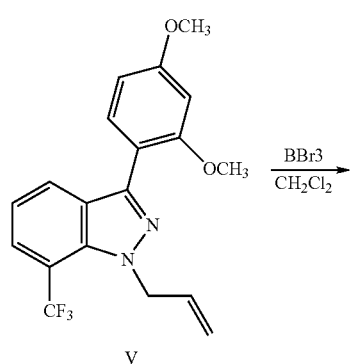
V

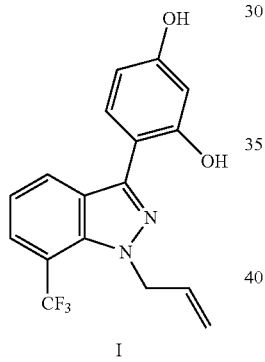
I

The synthetic route depicted above is generally advantageous to that shown in Scheme 2 at least with respect to the fact that it avoids the costly step of chromatography on silica gel.

Scheme 2.

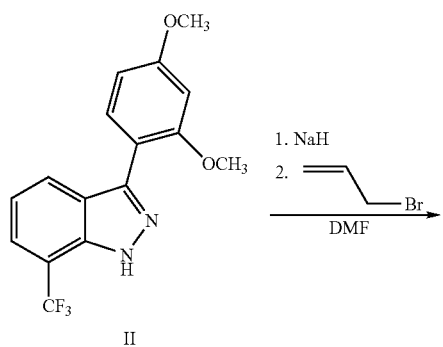
II

-continued

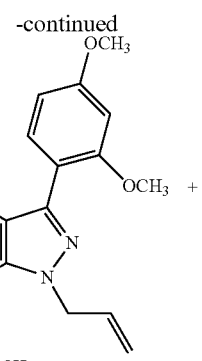

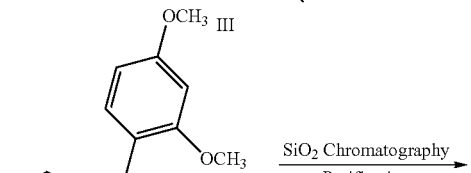

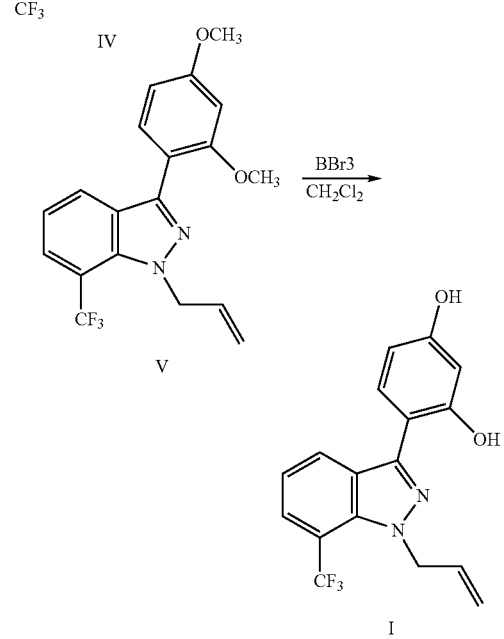
I

A mixture of methanol and water can optionally be used to recrystallize the compound of formula I. Such a formulation provides no residual solvent issues and the solvent ratios can be adjusted to optimize the yield.

The present invention may be further understood by the following non-limiting examples.

EXAMPLE 1

Synthesis of 1-Allyl-3-(2,4-dimethoxyphenyl)-7-trifluoromethyl-1H-indazole

Under an atmosphere of nitrogen, a 1.3 M tetrahydrofuran solution of lithium(trimethylsilyl)amide (1.26 L, 1.63 mol) was added to a cold (−15 to −10° C.) stirred solution of 3-(2,4-dimethoxyphenyl)-7-trifluoromethyl-1H-indazole (0.250 kg, 0.766 mol) in tetrahydrofuran (1.66 kg, 1.87 L) and dimethylformamide (0.227 kg, 0.240 L). The addition was carried out over 40-50 min and the temperature of the reaction mixture was maintained at −15 to −10° C. during the course of the addition. The reaction mixture was then warmed to 15-20° C. over about 1 hour. Allyl bromide (0.282 kg, 0.202 L, 2.33 mol) was added over 20-30 min. The temperature of the reaction mixture was maintained at 15-25° C. for 40-50 h. Anhydrous 2B alcohol (anhydrous ethanol with 0.5 to 0.6% by weight of toluene as a denaturant, 04.08 kg, 0.500 L) was then added to the reaction mixture. The resulting solution was concentrated by distillation (under atmospheric pressure) to a volume of about 2.1 L. An additional 0.408 kg (0.500 L) of anhydrous 2B alcohol was then added to the concentrate. The resulting solution was concentrated by distillation under atmospheric pressure to a volume of about 0.95 L. The stirred concentrate was first cooled to 15-20° C. over 3 h and then to 5-10° C. over 1 h. The mixture was stirred for 2 h at 5-10° C. The product mixture (1-allyl-3-(2,4-dimethoxyphenyl)-7-trifluoromethyl-1H-indazole and 2-allyl-3-(2,4-dimethoxyphenyl)-7-trifluoromethyl-1H-indazole) crystallized during this period. The product was then isolated by filtration, washed with cold (5-10° C.) 2B alcohol (2×0.3 L), and dried to a constant weight under reduced pressure (≦30 mm Hg) at 40-50° C. The yield of 1-allyl-3-(2,4-dimethoxyphenyl)-7-trifluoromethyl-1H-indazole was 0.18 kg (64% of theory).

EXAMPLES 2-8

Synthesis of 1-Allyl-3-(2,4-dimethoxyphenyl)-7-trifluoromethyl-1H-indazole

Examples 2-8 were performed under conditions essentially analogous to Example 1 except as noted in the table below. Ratios of 1-allyl-3-(2,4-dimethoxyphenyl)-7-trifluoromethyl-1H-indazole (II) to 2-allyl-3-(2,4-dimethoxyphenyl)-7-trifluoromethyl-1H-indazole (III) were determined by standard HPLC techniques.

| Ex. | Scale (g) | Base | Solvent | Allyl Bromide | Rxn time/ Temp. | Product Ratio III:II by HPLC |
|---|---|---|---|---|---|---|
| 2 | 1 | NaOH 3 eq. Bu$_4$NBr 0.1 eq. | CH$_2$Cl$_2$ 15x | 1.1 eq. | 1 h/rt. | 55:45 |
| 3 | 1 | TMP | DMF | 1 eq. | 1 h/100° C. | 49:51 (10% conversion) |
| 4 | 1 | KN(SiMe$_3$)$_2$ | THF | 1.1 eq. | 1 h/50° C. | 59:41 (90% conversion) |
| 5 | 1 | NaN(SiMe$_3$)$_2$ | THF | 1.1 eq. | 1 h/60° C. | 38:62 (8% conversion) |
| 6 | 1 | NaOH Bu$_4$NBr 0.1 eq | Toluene | 1.1 eq. | 0.5 h/60° C. | 57:43 |
| 7 | 1 | LiN(C$_6$H$_{11}$)$_2$ | THF | 4 eq. | 2 h/20-60° C. | No reaction |
| 8 | 1 | LiN(C$_6$H$_{11}$)$_2$ | THF/ 1 eq. HMPA | 3 eq. | 2 h/20° C. | 64:36 96% conversion |

EXAMPLES 9-29

Synthesis of 1-Allyl-3-(2,4-dimethoxyphenyl)-7-trifluoromethyl-1H-indazole

Examples 9-29 were performed under conditions essentially analogous to Example 1 except as noted in the table below. Ratios of 1-allyl-3-(2,4-dimethoxyphenyl)-7-trifluoromethyl-1H-indazole (II) to 2-allyl-3-(2,4-dimethoxyphenyl)-7-trifluoromethyl-1H-indazole (III) were determined by standard HPLC techniques.

| Ex. | Scale (g) | Base = LiN(SiMe$_3$)$_2$ | Solvent/ Reagent | Allyl Bromide/ Addition Time | Rxn Time/ Temp. | Product: Isomer by HPLC |
|---|---|---|---|---|---|---|
| 9 | 1 | 1.5 eq. | THF | 1.1 eq./ 1 min. | 2 h/20° C. | No reaction |
| 10 | 1 | 1.5 eq. | THF/ 1 eq. HMPA | 4 eq./ 5 min. | 2 h/20° C. | 68:32 99% conversion |
| 11 | 1 | 1.5 eq. | THF/ 8 eq. DMF | 3 eq./ 5 min. | 18 h/20° C. | 69:31 w/5% imp. 52% conversion |
| 12 | 1 | 1.5 eq. | THF/ 3 eq. DMPU | 3 eq./ 5 min. | 2 h/20° C. | 61:39 w/16% imp |

-continued

| Ex. | Scale (g) | Base = LiN(SiMe$_3$)$_2$ | Solvent/ Reagent | Allyl Bromide/ Addition Time | Rxn Time/ Temp. | Product: Isomer by HPLC |
|---|---|---|---|---|---|---|
| 13 | 1 | 1.5 eq. | THF/3 eq DMF 1 eq. DMPU | 3 eq./ 5 min. | 18 h/20° C. | 100% conversion 68:32 w/5% imp. |
| 14 | 1 | 3.0 eq. add. at −45° C. | THF | 2 eq./ 1 min. | 1-18 h/ 20° C. | 50% conversion 85:15 |
| 15 | 1 | 1.5 eq. add. at −25° C. | THF/ 1 eq. HMPA | 4 eq./ 2 h | 60 h/20° C. | 4% conversion 73:27 |
| 16 | 1 | 1.5 eq. add. at −25° C. | THF/ 3 eq. HMPA | 3 eq./ 5 min. | 1 h/20° C. | 99% conversion 62:38 |
| 17 | 1 | 1.3 eq. add. at −25° C. | THF/ 1 eq. HMPA | 4 eq./ 5 min. | 18 h/20° C. | 99% conversion 61:39 |
| 18 | 1 | 1.5 eq add. at −25° C. | THF/ 1 eq. HMPA | 3 eq./ 2 h | 18 h/20° C. | 100% conversion 67:33 |
| 19 | 1 | 1.5 eq. add. at −25° C. | THF/ 8 eq. DMF | 3 eq./ 5 min | 2 h/20° C. | 100% conversion 69:31 |
| 20 | 1 | 1.5 eq add. at −25° C. | THF/ 3 eq. DMPU | 3 eq./ 5 min. | 2 h/20° C. | 100% conversion 67:33 |
| 21 | 1 | 1.5 eq add. at −25° C. | THF/ 6 eq. DMF | 3 eq./ 1 h at rt. | 3 h/20° C. | 100% conversion 71:29 |
| 22 | 1 | 2.0 eq add. at −25° C. | THF/ 4 eq. DMF | 3 eq./0.5 h at rt. | 18 h/20° C. | 100% conversion 78:22 |
| 23 | 5 | 2.0 eq add. at −25° C. | THF/ 4 eq. DMF | 3 eq./0.5 h at rt. | 22 h/20° C. | 99.8% conversion 77:23 |
| 24 | 1 | 2.0 eq add. first | THF/ 4 eq. DMF | 3 eq./5 min at rt. | 18 h/20° C. | 99.5% conversion 76:24 |
| 25 | 0.5 | 3.0 eq add at −25° C. | THF/ 4 eq. DMF | 3 eq./ 5 min | 60 h/20° C. | 99.6% conversion 79:21 |
| 26 | 5 | 3.0 eq add. at −25° C. | THF/add last 6 eq. DMF | 3 eq./ 5 min | 60 h/20° C. | 99.7% conversion 80:20 |
| 27 | 1 | 2.5 eq add. at −25° C. | THF/add last 5 eq. DMF | 3 eq./ 5 min | 18 h/20° C. | 97% conversion 72:28 |
| 28 | 1 | 2.0 eq add. at 0° C. | THF/add last 4 eq. DMF | 3 eq./ 5 min | 19 h/20° C. | 98% conversion 73:27 |
| 29 | 1 | 2.0 eq add. at 25° C. | THF/add. last 4 eq. DMF | 3 eq./ 5 min | 19 h/20° C. | 99.5% conversion 73:27 80% conversion |

Abbreviations:
THF = tetrahydrofuran,
DMF = N,N-dimethylformamide,
HMPA = hexamethylphosphoramide,
DMPU = N,N'-dimethyl-N,N'-propylene urea,
TMP = 2,2,6,6-tetramethylpiperidine

EXAMPLE 30

Synthesis of 1-Allyl-3-(2,4-dimethoxyphenyl)-7-trifluoromethyl-1H-indazole

Example 30 was performed under conditions essentially analogous to Example 22 except for the use of allyl chloride in place of allyl bromide. Conditions and results are reported in the table below.

| Ex. | Scale (g) | Base | Solvent | Allyl Chloride | Rxn time/ Temp. | Product: Isomer by HPLC |
|---|---|---|---|---|---|---|
| 30 | 1 | 2.0 eq LiN(SiMe$_3$)$_2$ add. at −25° C. | THF/ 4 eq. DMF | 3 eq. allyl chloride/ 0.5 h at rt. | 18 h/ 20° C. | No reaction |

EXAMPLE 31

Synthesis of 4-[1-allyl-7-(trifluoromethyl)-1H-indazol-3-yl]benzene-1,3-diol 1-Allyl-3-(2,4-dimethoxyphenyl)-7-(trifluoromethyl)-1H-indazole (0.065 g, 0.18 mmol) was treated with boron tribromide (0.136 mL, 1.4 mmol) and 1.0 mL of cyclohexene at −78° C. and then slowly allowed to warm to ambient temperature. The reaction was quenched by dropwise addition of methanol to the cooled reaction. The solvent was removed and the residue portioned with EtOAc and 1N HCl. The organic phase was washed with brine and dried with Na$_2$SO$_4$). Removal of the solvent in vacuo afforded the crude product. Pure product was obtained by crystallization to give the product (0.066 g) as a white solid, mp 114-115° C.;

$^1$H NMR (DMSO-d$_6$): δ 4.87 (dd, 1H, J=1.37 and 17.10 Hz), 5.31-5.08 (m, 3H), 6.01-6.08 (m, H), 6.39 (dd, 1H, J=2.44 and 8.40 Hz), 6.46 (s, 1H), 7.30 (t, 1H), 3.78 (d, 1H), 7.85-7.87 (m, 1H), 8.14-8.19 (m, 1H), 9.59 (broad s, 1H), 9.82 (broad s, 1H) MS (ESI) m/z 335 [M+H]+. Anal. calcd for C$_{17}$H$_{13}$F$_3$N$_2$O$_2$: C, 61.08; H, 3.92 N, 8.38. Found: C, 61.02; H, 3.76 N, 8.28.

EXAMPLE 32

Isolated compound I was found to contain the regioisomer (VI) at a level of approximately 0.21% as determined by $^{19}$F nmr at 512X× expansion. The relative solubility in a mixture of methanol and water (57:43 v/v) was determined to be 6 mg/mL for compound I and 140 mg/mL for the regioisomer (VI), thus showing a 20× difference in favor of the impurity.

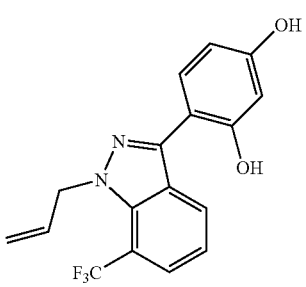

I

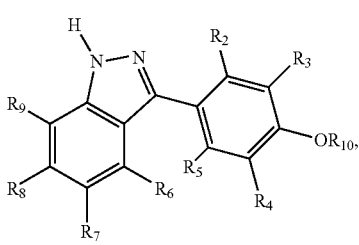

VI 100 mg of compound I, containing the isomer VI was crystallized from methanol/water (1 mL; 57/43 v/v). $^{19}$F nmr of the recrystallized product showed a peak for compound I but no visible peak for the isomer VI at 512× expansion.

All patents, publications, and other documents cited herein are hereby incorporated by reference in their entirety.

What is claimed is:

1. A process comprising:
contacting a compound of the formula:

wherein:
R$_2$, R$_3$, R$_4$, and R$_5$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CN, —NO$_2$, —CHO, or —CO$_2$R$_{11}$;
R$_6$, R$_7$, R$_8$, and R$_9$, are each, independently, hydrogen, alkyl of 1-6 carbon atoms, alkenyl of 2-7 carbon atoms, hydroxy, alkoxy of 1-6 carbon atoms, aryloxy of 6-20 carbon atoms, halogen, trifluoromethyl, —CO$_2$R$_{11}$, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S;

$R_{10}$ is hydrogen, alkyl of 1-6 carbon atoms, —$CO_2R_{11}$, —$CONHR_{11}$, —$P(=O)(OH)OR_{11}$, —$CO(CH_2)_nCH(NHR_{12})CO_2R$, or a hydroxyl protecting group;

$R_{11}$ is hydrogen, alkyl of 1-6 carbon atoms, aryl of 6-20 carbon atoms, or arylalkyl of 7-26 carbon atoms;

$R_{12}$ hydrogen or —$CO_2R_{11}$; and n=0-3;

with lithium bis(trimethylsilyl)amide, lithium dicyclohexylamide, or potassium bis(trimethylsilyl)amide in the presence of a dipolar aprotic solvent to produce a first reaction mixture;

contacting the first reaction mixture with a compound of the formula $R_1$—X, where:

$R_1$ alkyl of 1-6 carbon atoms, alkenyl of 2-7 carbon atoms, cycloalkyl of 3-8 carbon atoms, cycloalkenyl of 4-8 carbon atoms, aryl of 6-20 carbon atoms, arylalkyl of 7-26 carbon atoms, or a saturated, unsaturated, or partially unsaturated heterocyclic ring or ring system of 4-14 atoms, containing 1-4 heteroatoms selected from N, O, and S; and X is a leaving group;

to produce a second reaction mixture;

mixing the second reaction mixture with at least one alcohol;

optionally cooling the second mixture below ambient temperature;

precipitating a compound of the formula:

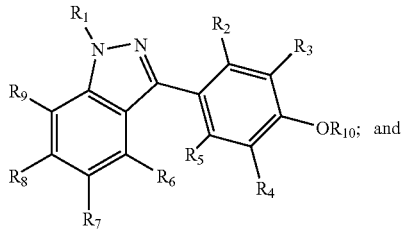

isolating the precipitated compound.

2. The process of claim 1 wherein said alcohol is methanol, ethanol, 1-propanol, 2-propanol, or mixtures thereof.

3. The process of claim 1 wherein X is Cl, Br, or I.

4. The process of claim 2 wherein said alcohol is ethanol.

5. The process of claim 1 wherein the solvent comprises tetrahydrofuran.

6. The process of claim 5 wherein the solvent further comprises an additional component, that component being a polar organic solvent.

7. The process of claim 6 wherein the polar organic solvent is dimethylformamide (DMF), hexamethyphosphoramide (HMPA), N,N'-dimethyl-N,N'-propylene urea (DMPU), or 2,2,6,6-tetramethylpiperidine (TMP).

8. The process of claim 7 wherein the solvent further comprises DMF.

9. The process of claim 1 wherein the second reaction mixture is cooled to a temperature of 10° C. or below to produce the precipitate.

10. The process of claim 1 wherein at least a portion of the solvent is removed prior to cooling the second reaction mixture to produce the precipitate.

11. The process of claim 10 wherein at least one half by weight of the solvent is removed prior to cooling the second reaction mixture to produce the precipitate.

12. The process of claim 4 wherein the ethanol is anhydrous.

13. The process of claim 1 further comprising washing the precipitate with ethanol at a temperature of 10° C. or below to produce a washed precipitate.

14. The process of claim 13 further comprising drying the washed precipitate.

15. The process of claim 1 wherein $R_1$ is allyl, $R_2$ is $OCH_3$, $R_3$-$R_8$ are each H, and $R_{10}$ is $CH_3$.

16. The process of claim 1 wherein $R_2$ is an alkoxy of 1-6 carbon atoms and $R_{10}$ is an alkyl of 1-6 carbon atoms.

17. The process of claim 16 further comprising converting $R_2$ to OH and $R_{10}$ to H to produce a compound of the formula:

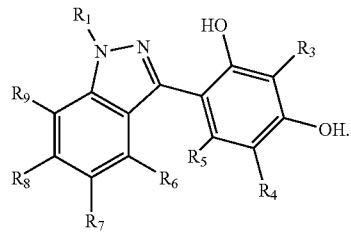

18. The process of claim 17 where the conversion of $R_2$ to OH and $R_{10}$ to H is accomplished by base hydrolysis, acid hydrolysis, or hydrogenation.

19. The process of claim 18 wherein the conversion of $R_2$ to OH and $R_{10}$ to H is accomplished by acid hydrolysis in the presence of $BBr_3$ or a mixture of $BBr_3$ and $BCl_3$.

20. The process of claim 17 wherein $R_1$ is allyl and $R_3$-$R_8$ are each H.

21. The process of claim 17 wherein $R_1$—X is allyl bromide.

* * * * *

UNITED STATES PATENT AND TRADEMARK OFFICE
CERTIFICATE OF CORRECTION

PATENT NO. : 7,601,847 B2  Page 1 of 1
APPLICATION NO. : 11/257344
DATED : October 13, 2009
INVENTOR(S) : Considine et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 874 days.

Signed and Sealed this

Fifth Day of October, 2010

David J. Kappos
*Director of the United States Patent and Trademark Office*